(12) United States Patent
Canal Vila et al.

(10) Patent No.: US 11,747,247 B2
(45) Date of Patent: Sep. 5, 2023

(54) MEMBRANE STRUCTURE SUITABLE FOR A SAND PRODUCTION TEST

(71) Applicant: REPSOL, S.A., Madrid (ES)

(72) Inventors: Jacobo Canal Vila, Madrid (ES); José Alvarellos Iglesias, Madrid (ES); Nubia Aurora González Molano, Madrid (ES); Jorge Delgado Martín, A Coruña (ES); María del Carmen García García, A Coruña (ES)

(73) Assignee: REPSOL, S.A.

( * ) Notice: Subject to any disclaimer, the term of this patent is extended or adjusted under 35 U.S.C. 154(b) by 47 days.

(21) Appl. No.: 17/541,470

(22) Filed: Dec. 3, 2021

(65) Prior Publication Data

US 2022/0196528 A1   Jun. 23, 2022

(30) Foreign Application Priority Data

Dec. 23, 2020  (EP) .................................... 20383147

(51) Int. Cl.
*G01N 3/12* (2006.01)
*G01N 3/02* (2006.01)
(Continued)

(52) U.S. Cl.
CPC ............... *G01N 3/12* (2013.01); *G01N 3/02* (2013.01); *G01N 3/10* (2013.01); *G01N 15/0806* (2013.01);
(Continued)

(58) Field of Classification Search
CPC .. G01N 3/12; G01N 3/02; G01N 3/10; G01N 15/0806; G01N 33/24; G01N 2203/0256
See application file for complete search history.

(56) References Cited

U.S. PATENT DOCUMENTS

| 10,197,549 B2* | 2/2019 | Thomas ................... E21B 33/14 |
| 2010/0089124 A1* | 4/2010 | Katti ....................... E02D 1/027 73/38 |

(Continued)

FOREIGN PATENT DOCUMENTS

| CN | 112284922 A | * | 1/2021 | |
| CN | 112880549 A | * | 6/2021 | ............... G01B 7/18 |

OTHER PUBLICATIONS

Gonzalez Molano, N.A., et al., Experimental and Numerical Characterization of the Stress-Strain Behavior or Weak Sandstone Formations for Sanding Assessment, Proceedings of the ASME 2018 37th Intl. Conf. on Ocean, Offshore and Arctic Eng., OMAE2018, Jun. 17-22, 2018, Madrid, Spain, V008T11A003.

(Continued)

*Primary Examiner* — Ryan D Walsh
(74) *Attorney, Agent, or Firm* — Tristan A. Fuierer; Casimir Jones, SC

(57) ABSTRACT

The invention provides a membrane structure suitable for a sand production test of a rock sample provided with a hollow cylinder shape, the membrane structure comprising a main body with a housing configured to confine the rock sample within; a watertight outer wall adapted to withstand external hydrostatic pressure exerted by a first fluid; a permeable inner wall limiting the housing and configured to exert pressure on the rock sample and, to inject a second fluid into the outer surface of said rock sample; a plurality of internal hollow chambers located between the watertight outer wall and the permeable inner wall, wherein each one of the plurality of internal hollow chambers includes a plurality of rigid particles filling the inner space of each hollow chamber for transmitting the external pressure exerted from the outer wall to the inner wall.

15 Claims, 9 Drawing Sheets

(51) Int. Cl.
    *G01N 33/24* (2006.01)
    *G01N 3/10* (2006.01)
    *G01N 15/08* (2006.01)
(52) U.S. Cl.
    CPC ..... *G01N 33/24* (2013.01); *G01N 2203/0256* (2013.01)

(56) References Cited

U.S. PATENT DOCUMENTS

2015/0111716 A1* 4/2015 Hakimuddin ........ G01N 33/241
                                                494/10
2018/0335374 A1   11/2018 Kanj

OTHER PUBLICATIONS

European Search Report, EP 20383147, dated Jun. 8, 2021.

* cited by examiner

MEMBRANE STRUCTURE SUITABLE FOR A SAND PRODUCTION TEST

CROSS-REFERENCE TO RELATED APPLICATIONS

This application is filed under 35 U.S.C. § 119(a) and claims priority to European Patent Application No. EP20383147.4, filed 23 Dec. 2020 and entitled "Membrane Structure Suitable for a Sand Production Test" in the name of Jacobo CANAL VILA et al., which is incorporated herein by reference in its entirety.

FIELD OF THE INVENTION

The present invention belongs to the technical field of oil and gas production, more specifically to the field of drilling operations. In particular, the invention relates to detailed characterization and properties prediction of boreholes by means of sand production tests of rock samples for quantitatively determining sand production rate over time, based on applied forces and fluid flow rate.

More in particular, the invention provides a membrane structure provided with internal hollow chambers which can be filled with a fluid which allow to apply different pressure on specific portions of the rock sample resulting in true 3D tensional stress also known as true triaxial test while providing a flow of said fluid to said rock sample.

PRIOR ART

In the oil and gas industry, sand production is a well-known phenomenon associated to borehole drilling and hydrocarbon fluids production operations. Essentially, it involves the production and transportation of solid particles into the borehole and to the surface together with the flow of reservoir fluids, which results in a series of undesired consequences that may impact significantly the whole production project, from both a development and exploitation perspectives.

Sand particles production is a consequence of the failure of the rock surrounding a borehole (which leads to the subsequent detachment of the sand grains) which takes place when the stress induced mainly during drilling and/or the fluid flow drag force exceeds the formation strength. In particular, the pressure gradient generated between the reservoir pressure and the borehole flowing pressure may cause sand particles detachment. In this sense, the production of hydrocarbon fluids causes frictional pressure and forces, proportional to the viscosity and flow rate of said fluids, which may exceed the borehole compressive strength.

Another key factor related with the sand production phenomenon in boreholes is the presence of water. The ratio of water produced (water-cut) in comparison with the total amount of hydrocarbon fluids produced may have a great impact in the failure of the perforated rock that leads to the detachment of sand particles. The sand production increases as the water-cut increasing.

Water breakthrough leads to an increase in the water saturation of the rock material surrounding the borehole, which in turn involves a reduction in capillary cohesion. In particular, when the rock formation, i.e., the borehole, is water-wet, some of the particles cohesion is provided via capillarity.

In other words, said particles are bound partly due to the surface tension of connate water that surrounds each solid particle. When water is generated, water saturation is increased thereby, causing the connate water to adhere said generated water, destroying capillary cohesion, thus reducing the surface tension force, which leads to reduce the particles cohesion.

Further, water breakthrough also implies relative permeability changes in the rock surrounding the borehole. These changes may alter the pressure distribution and, thus, local stresses, further contributing to the aforementioned cohesion loss and sand production rock failure.

In particular, as the water-cut increases, the relative permeability of the hydrocarbon fluid decreases, what causes an increase in the differential pressure required for maintaining a given flow rate for said hydrocarbon fluid. This increase of the differential pressure in the rock formation surrounding the borehole leads to a respective increase of the shear force through the borehole.

Consequently, the undesired presence of these solid particles detached from the borehole involves a series of drawbacks that makes the teams in charge of developing the drilling operations to face a challenging scenario.

The solid particles tend to accumulate, among others, in the surface of tools, boreholes, or pipelines, resulting in a reduction of the hydrocarbon fluid production. The sand accumulated in the borehole may cause agglomeration or clustering of particles (sand plugs) that, if not cleared, may collapse and obstruct the production.

In view of the aforementioned drawbacks, different design tools and analysis methods have been developed to evaluate and quantify the risk of sand production. Testing equipment have been used in laboratory trying to reproduce true triaxial compression under various environmental conditions that may take place during borehole operation which may lead to sand production.

These tests are typically performed using rock samples with a cylindrical shape which simulates actual loading conditions under downhole stresses, as well as with pressing oil and brine as flowing fluid in order to investigate the effects of water breakthrough on the amount of produced sand. Accordingly, triaxial rock testing allows to predict the mechanical behavior (borehole stability) and estimate sand production; however, current tests do not allow to differentiate the pressure applied to the sample of rock according to an angle measured in a plain perpendicular to the main axis of the cylindrical sample limiting the true triaxial tensional state caused on the sample.

Typically, this sand production testing equipment comprises a sanding cell which houses the cylindrical rock sample within. This sanding cell may comprise a membrane or sleeve structure configured for establishing direct mechanical contact with the rock sample. This contact allows to transmit radial pressure exerted by a confining fluid supplied into a closed chamber which is configured for watertightly housing the sanding cell within. Further, said membrane or sleeve may be configured so as to permit a fluid to flow towards the inner volume where the rock sample is confined.

Additionally, a loading frame is provided and configured for applying axial pressure to the rock sample, along with a plurality of instrumentation and sensing means in charge of carrying out the corresponding measurements.

Typical maximum values for the parameters used can be the following:

Maximum operating axial stress: 11,000 psi;
Maximum operating confining pressure: 5000 psi;

Wherein 1 psi (pound per square inch) is equal to 6894.76 Pa (Pascal, N·m-2).

DESCRIPTION OF THE INVENTION

The present invention provides a solution for the aforementioned problems by a membrane structure suitable for a sand production test of a rock sample according to claim 1 and a system suitable for a said sand production test of a rock sample according to claim 10. Advantageous embodiments are defined in the dependent claims.

All the features described in this specification, including the claims, description and drawings, can be combined in any combination, with the exception of combinations of such mutually exclusive features.

According to a first inventive aspect, the invention provides a membrane structure suitable for a sand production test of a rock sample provided with a hollow cylinder shape extended along a longitudinal direction, the membrane structure comprising a main body, wherein the main body comprises:

- a housing (H) configured to confine the rock sample within;
- a watertight outer wall adapted to withstand external hydrostatic pressure exerted by a first fluid when the membrane structure is in operative manner;
- a permeable inner wall limiting the housing and configured to exert pressure on the rock sample and, to inject a second fluid into the outer surface of said rock sample when the membrane structure is in operative manner;
- a first base;
- a second base opposite to the first base according to the longitudinal direction;
- a plurality of internal hollow chambers located between the watertight outer wall and the permeable inner wall, wherein

- the main body of the membrane structure comprises a plurality of partition walls, each one of the plurality of partition walls being configured for separating two adjacent internal hollow chambers;
- the first base or the second base of the main body comprises a plurality of inlets, each one being configured for establishing a fluidic communication between one of the plurality of internal hollow chambers and an external source of the second fluid; and
- each one of the plurality of internal hollow chambers comprises a plurality of rigid particles filling the inner space of each hollow chamber, said plurality of rigid particles intended for transmitting the external pressure exerted from the outer wall to the inner wall while allowing the passage of the second fluid from the at least one inlet to the permeable inner wall.

The membrane structure of the invention is part of the testing equipment required for carrying out a sand production test on a rock sample. As aforementioned, said tests consisting essentially of applying axial pressure, typically by means of a piston, and radial pressure in the form of hydrostatic pressure exerted by a confining fluid, while providing a flow of a second fluid, typically brine, onto the outer surface of the rock sample.

More in particular, the membrane structure is the part of the sanding cell, wherein the rock sample is confined within, which is configured for establishing mechanical contact with said rock sample.

With regard to the rock sample, it will be understood that, in order to reproduce operating conditions of a borehole, it is provided in the form of a hollow cylinder, that is, with an annular cylindrical shape.

Accordingly, the membrane structure of the invention comprises a main body adapted to adjust to the outer contour of the rock sample so as to contact with it along its surface. That way, hydrostatic pressure exerted by a first fluid, (i.e., the confining fluid) on the main body of the membrane structure is transmitted for providing the rock sample with the radial components of the tensional stresses.

In particular, on one side the main body of the membrane structure comprises a watertight outer surface adapted to withstand said hydrostatic pressure exerted by the first fluid. Typically, said first fluid is a pressing oil.

On the other side, the main body of the membrane structure comprises a permeable inner wall limiting (i.e., defining) the circular boundary of the housing wherein the rock sample is confined during operation, said permeable inner wall being configured for transmitting the aforementioned hydrostatic pressure, withstood by the watertight outer wall, onto the rock sample, and to inject a second fluid onto the outer surface of said rock sample.

Additionally, the main body of the membrane structure comprises a plurality of internal hollow chambers. These internal hollow chambers are compartments separate from each other by means of a plurality of partition walls. In other words, the whole internal hollow volume of the main body is partitioned, i.e., divided, by said partition walls which, besides dividing the internal hollow volume into respective hollow chambers, serve to differentiate the pressure exerted by each internal hollow chamber allowing to cause a true triaxial tensional stress in the sample of rock. Additionally, partition walls are structural ribs which contribute to distribute and withstand the tensional state induced in the main body of the membrane structure by the first and second fluid pressure forces. According to a preferred embodiment, partition walls are arranged equally distributed according to the perimetral length allowing to determine the pressure exerted at different angles according to a plane perpendicular to the main axis of the sample of rock.

In this sense, in order to allow transmission of the hydrostatic pressure exerted by the first fluid, and withstood by the watertight outer wall, through the empty spaces of the chambers, said internal hollow chambers are in-filled with a plurality of rigid particles. In a preferred embodiment, the internal hollow chambers are filled with high strength grit or ball bearings. Said rigid particles stack so as to fill the volume of the internal hollow chambers partially, that is, bridging the watertight outer wall and the permeable inner wall so as to transmit force between them, while leaving empty interstices among them so as to let the second fluid access each hollow chamber.

Each of these internal hollow chambers is provided with a respective inlet to receive the second fluid. As indicated previously, the presence of the second fluid changes the pore pressure, which in turn modifies the stresses, and so the tensional state depending on the internal hollow chamber, causing rock deformation and failure, leading to sand production. In this regard, the partition wall is permeable so as to let the second fluid flow under pressure inward radially, that is, towards the rock sample, to simulate conditions of water breakthrough.

This effect allows analyzing the influence of the presence of the second fluid in the phenomenom of sand production, and to apply a differential pressure around the outer surface of the rock sample thanks to the operational independence among each internal hollow chamber. In particular, as it has been previously disclosed thanks to the second fluid flowing through each internal hollow chamber at different pressures, it is possible to apply different pressure on specific sides of the rock sample, thus providing a so-called pluriaxial (or true triaxial) test In preferred embodiment, said second fluid is water or brine.

The main body of the membrane structure comprises a first base and a second base opposite to the first base according to the longitudinal direction. It is in the first base wherein the plurality of inlets, which establish fluidic communication between an external source of the second fluid and the internal hollow chambers, are provided.

Both the first and the second base are adapted for abutting respective base plates of a sand production system for watertightly closing the internal volume of the membrane structure (i.e., the housing), wherein the rock sample is confined. This way, crossed leakage is prevented, that is, leakage of the second fluid out of the housing, or leakage of the first fluid (i.e., the confining fluid) which applies pressure over the watertight outer wall, inside the housing.

As aforementioned, many factors contribute to sand production, such as the degree of anisotropy between the in situ stresses, the rock elastic and strength properties, or water breakthrough. Therefore, the membrane structure of the invention provides a better numerical understanding of the borehole behavior thanks to an improved hydromechanical coupling that allows to reproduce dynamic changes of stresses and rock deformation due to pore pressure changes at different locations in the near-wellbore region (i.e., a non-uniform pressure profile from the formation to the well.

In view of the aforementioned advantageous technical effects, the membrane structure of the invention allows sand production tests to be performed simulating a more complete distribution of the forces in hydrocarbon reservoir exploitation, what, in turn, improves the feedback and knowledge on sand behavior in the near-borehole regions obtained for supporting operational development.

In a particular embodiment, the permeable inner wall (112) comprises a plurality of pores (112.1) such that fluidic communication is established between each one of the plurality of internal hollow chambers (115) and the housing (H) configured to confine the rock sample (300).

Permeability is achieved through said pores, or perforations, which establish fluidic communication between each one of the internal hollow chambers with the internal volume (i.e., the housing (H)) destined to house the rock sample within.

Having this configuration, of fluidic communication established through pores connecting separated volumes allows defining, in the build-up phase of the membrane structure, by means of the number, distribution pattern, and diameter of pores, the way in which the second fluid is supplied to the interior of the housing (H), that is, the way it is provided onto the rock sample.

In a particular embodiment, the watertight outer wall is covered by a reinforcing sleeve. Said reinforcing sleeve provides the main body of the membrane structure with additional stiffness by wrapping (i.e., covering) it around its outer contour, increasing the thickness of the membrane structure thereby.

In a more particular embodiment, the reinforcing sleeve has a thickness of 3 mm.

In a particular embodiment, at least one of the plurality of internal hollow chambers extends along a circular trapezoidal section of the main body.

In a particular embodiment, the plurality of internal hollow chambers is equidistributed along a circular path around the longitudinal direction.

The main body of the membrane structure according to a preferred embodiment is shaped as a hollow cylinder. In this regard, the cross-section of the membrane structure is an annulus. Accordingly, an internal hollow chamber can be shaped with a circular trapezoidal cross-section, whose boundaries are thus defined by:
- a first inner surface contained in a cylindrical section of the main body with a radius R, smaller than the radius of the watertight outer wall;
- a second inner surface contained in a cylindrical section of the main body with a radius r, smaller than R and greater than the radius of the permeable inner wall; and
- lateral surfaces comprised in respective radial planes, said lateral surfaces corresponding with sides of the two respective partition walls that separate the internal hollow chamber from adjacent internal hollow chambers.

This geometric configuration with radial symmetry provides the membrane structure with an optimal internal stress distribution capacity that results in a high degree of isotropy with respect to the contribution generated, to the resulting tensional state, by the hydrostatic pressure exerted by the first fluid on the outer watertight wall.

In a particular embodiment, the plurality of rigid particles are steel spherical particles stacked in a close-packing configuration.

By selecting, during the design and build-up phase, the size of the rigid particles and the packing structure, it is possible to optimize the mechanical properties of the internal hollow chambers and of the whole membrane structure thereby.

In particular, the density of the rigid particles housed inside the internal hollow chambers can be increased, while allowing the second fluid to flow inside, given that said second fluid will remain housed in the interstitial void spaces.

The presence of the steel spherical particles, stacked according to a close-packing configuration, provides stiffness to the main body of the membrane structure, bridging the watertight outer wall and the permeable inner wall, for an optimal transmission of the hydrostatic pressure exerted by the first fluid, without distorting the tension state resulting from steel spherical particles concentration gradients.

In a preferred embodiment, the steel spherical particles are stacked according to a hexagonal close-packed lattice. Advantageously, the stiffness tensor is transversely isotropic, that is, the transmission of stresses through cross-sectional planes according to the longitudinal direction of the hollow cylindrical shape of the membrane structure is optimal.

In a preferred embodiment, the diameter of the steel spherical particles is between the range of 1.25-1.70 mm.

In a particular embodiment, at least one internal hollow chamber (115) comprises a filtering mesh (115.2) provided next to the permeable inner wall (112).

The presence of the filtering mesh prevents the rigid particles housed within the internal hollow chambers from jeopardizing the supply of second fluid from the internal hollow chambers to the rock sample through the permeable inner wall.

In a more particular embodiment, wherein said permeable inner wall comprises a plurality of pores, the filtering mesh prevents the rigid particles from obstructing the pores through which the fluid is supplied to the rock sample.

In a preferred embodiment, said filtering mesh has a sieve size smaller than 0.5 mm.

In a particular embodiment, the main body comprises at least one radial hole configured to house a pin connected to an extensometer, allowing the access of the pin through an opening provided at the watertight outer wall to the inner wall for measuring the radial deformation of said sample or rock.

In a particular embodiment, the radial hole extends through a partition wall of the main body.

The use of extensometers allows to analyse the deformation of the rock sample during the sand production test. In particular, pins of a cantilever extensometer can be housed within said radial holes, for accessing the interior of the main body of the membrane structure and evaluate deformation of the outer surface of the rock sample.

In a particular embodiment, these holes comprise:
an opening provided at the watertight outer wall;
an internal channel extending through a partition wall of the main body,
a distal end located proximate to the rock sample, that is, in a section of the main body (110) with a radius slightly greater than the radius of the permeable inner wall.

In this way, the distal end of the pins mechanically contact the region of the membrane structure near the outer surface of the rock sample, but preventing establishing fluidic communication between the housing (H) wherein the rock sample is confined and the exterior of the membrane structure, which would cause crossed leakage of the first and second fluids.

According to this configuration, and opposite to the traditional concept according to which only deformations of the internal surface of the perforated rock sample were measured, deformations of the outer surface of the rock sample can be measured during the test. Said deformations are consequence of the resulting differential pressures applied to the outer surface of the rock sample as a contribution of the hydrostatic pressure exerted by the first fluid and transmitted by the membrane structure, and the partial contributions of each internal hollow chamber filled with the second fluid. These deformations are translated into linear displacements of the pins.

Therefore, said pins housed within the radial holes of the main body of the membrane structure, as indicated above, move linearly, being able to transmit the movement to an extensometer mounted on a column-type support structure, located facing the radial hole, which will provide information related to the deformation of the rock sample in the form of an electrical variation.

In a particular embodiment, the main body comprises a plurality of parallel radial holes lined up in a row, for obtaining information related to the deformation of the outer surface of the rock simple according to a longitudinal direction.

In a particular embodiment, the main body is made of an elastomeric polymer.

In a preferred embodiment, the elastomeric polymer the main body of the membrane structure is made of is provided by an Additive Manufacturing process.

Additive Manufacturing (AM), also referred to as 3D printing, relates to current manufacturing methods and technologies wherein three-dimensional components are built up applying successive layers of material under computer control, departing from a digital model of the component to be produced.

Typically, a meltable material changes to a liquid upon the application of heat and solidifies (or hardens) to a solid when cooled. Commonly, these AM technologies use a computer with 3D modelling software (Computer Aided Design or CAD), an additive manufacturing tool (e.g. machine equipment) and filaments of layering material. The CAD sketch is a 3D electronic model of the final 3D object built. The AM tool is able to read in data from the CAD file (both the cross-section geometry and surface pattern) and lays down or deposits successive filaments (then forming up layers) of liquid, powder, sheet material or the like, by at least one head in a layer-upon-layer fashion to fabricate a 3D object.

Additionally, before printing, the digital CAD sketch of the fitting is digitally sliced into multiple horizontal sections or layers. The printer controller then uses this generated slicing to manufacture the fitting sequentially, for instance with one layer at a time (i.e., layer-by-layer), with each layer adhering or bonding to the previous one.

Many technologies are encompassed within Additive Manufacturing technologies, depending on the form of the material and machine technology used, being the most relevant, among others: Stereolithography (SLA), Fused Deposition Modelling (FDM) or Fused Filament Fabrication (FFF), Multi-Jet Modelling, or Selective Laser Sintering (SLS).

Advantageously, manufacturing the main body of the membrane structure employing one of the aforementioned AM techniques 3D printing allows the creation and manufacture of geometries impossible for traditional methods to produce, either as a single part, or at all. Such geometries include hollow cavities within solid parts and parts within parts.

The nature of 3D printing allows the step-by-step assembly of the part or product, which guarantees enhancement of the design and better quality parts/products.

As mentioned above relative to quality, traditional manufacturing processes can result in a percentage of a batch of parts being defective or inconsistent in quality compared to the rest of the parts.

In 3D printing, the parts are printed in succession. Each successive individual part can be monitored, allowing errors to be caught in real time, reducing the overall number of failed parts and wasted materials while increasing consistent quality of the parts produced.

In a more preferred embodiment, the elastomeric polymer used for producing the main body of the membrane structure is Thermoplastic Polyurethane (TPU).

In a second inventive aspect, the invention provides a system suitable for a sand production test of a rock sample provided with a hollow cylinder shape extended along a longitudinal direction, the system comprising:
a first base plate;
a membrane structure according to an embodiment of the first inventive aspect, the second base of the membrane structure resting on the first base plate;
a second base plate resting on the first base of the membrane structure configured for exerting axial force to the membrane structure and to the rock sample confined within the housing of the membrane structure in operative manner;
a casing located over the first base plate, the casing configured for housing the membrane and the second base plate with an intermediate space between the casing and the membrane for housing the first fluid;
a piston adapted to exert axial force to the second base plate according to the longitudinal direction;
a first pump for pumping the first fluid;

a second pump for pumping the second fluid;
wherein the second base plate comprises at least an input port for the second fluid and an output port for the second fluid, such that
  the input port is in fluid communication with the second pump; and
  the output port is in fluid communication with the at least one inlet of the membrane structure configured for establishing a fluidic communication between the plurality of internal hollow chambers and an external source of the second fluid; and wherein the first pump is in in fluidic communication with the intermediate space of the casing for increasing the first fluid pressure, the first fluid being in contact with the watertight outer wall of the membrane structure in operative manner.

This system which comprises a membrane structure according to an embodiment of the first inventive aspect can be used for carrying out a sand production test which reproduces triaxial compression under various environmental conditions that may take place during borehole operation which may lead to sand production, thus allowing to obtain an optimal prediction of the mechanical behavior of the borehole and estimate sand production.

Said membrane structure is watertightly fixed to the first base plate by its second base. The second base plate is watertightly fixed to the first base of the membrane structure, so that the sanding cell wherein the rock sample is confined within is defined, closing the inner volume (i.e., the housing (H) of the membrane structure) thereby. Given that these are the elements of the system in mechanical contact with the rock sample, they are responsible for ultimate application of the forces configured for reproducing operational conditions, and thus, responsible for defining the tensional state of the rock sample.

In this sense, the second base plate is provided with a flow of the second fluid, by means of at least an input port in fluidic communication with corresponding pumping means, a flow which is redirected and channelled to the internal hollow chambers. More in particular, the second base plate is adapted for establishing fluidic communication with each of the inlets of said internal hollow chambers by means of corresponding output ports located in the very own first base plate, so that the second fluid is properly distributed to each internal hollow chamber.

As aforementioned, the watertight outer wall of the membrane structure withstands hydrostatic pressure exerted by a first fluid, typically a pressure oil, which is provided by the first pump. In particular, the first pump is in in fluidic communication with the intermediate space defined between the sanding cell and the casing. More in particular, the casing closes watertightly over the first base plate, thus defining a pressure chamber, for increasing the first fluid pressure provided therein by said first pump.

This way, the watertight outer wall receives the pressing oil which is under hydrostatic pressure providing radial components of the tensional stress to the rock sample, said radial components being transmitted through the main body of the membrane structure.

Finally, in order to reproduce completely the tensional state of the rock sample corresponding to the operating conditions of a borehole, the system comprises a piston that provides axial stress to the rock sample. In particular, the piston is configured to exert axial force on the second base plate. The combination of the axial stress and the radial components of the stress controlled by means of the hydrostatic pressure exerted by the first fluid, plus differential contributions of each internal hollow chamber, providing a flow of the second fluid to the rock sample, may provide a tensional stress under predefined conditions.

In a particular embodiment, sealing means can be provided at the joint interfaces between the first and/or second base of the membrane structure and the first and/or second base plate of the system, respectively, in order to increase the sealing effect that prevents cross-leakage between the internal housing where the rock sample is housed and the external pressure chamber defined by the casing, where the first fluid is confined.

In a more particular embodiment, the system comprises an O-ring seal provided at at least one of said joint interfaces.

In a particular embodiment, the system comprises at least one rigid fastening member comprising a first and a second distal ends, wherein the distribution base plate comprises a first anchoring point;
  the annular distribution disk comprises a second anchoring point;
and wherein
the at least one rigid fastening member is fixed:
  to the first anchoring point by the first distal end; and
  to the second anchoring point by the second distal end.

In a more particular embodiment, both anchoring points comprise threaded holes; the rigid fastening member is a rod; and both distal ends comprise respective threaded sections configured to engage each respective threaded hole, removably fixing the rigid fastening member thereto.

Through this configuration, prestressing can be provided to the sanding cell, in such a way that the first and second base plates are brought closer to the first and second bases of the membrane structure, respectively, so that pressure is applied. Therefore, stability is provided to the assembly prior to the development of the sand production test, further increasing the sealing effect between parts, in such a way as to help prevent cross-leakage between the internal housing where the rock sample is housed and the external pressure chamber where the first fluid is confined.

In a particular embodiment, the fluid communication between the second pump and the input port of the second base plate is established by means of a distribution piping, such that
  the distribution piping is coupled at a first end with the input port of the second base plate; and
  the distribution piping is coupled at a second end with the first base plate; and wherein the first base plate further comprises a second input port configured for establishing fluid communication between the second pump and the second end of the distribution piping.

In a particular embodiment, the piston is coupled to a truncated cone resting on the second base plate and configured for pressure redistribution, to the second base plate, of the axial force exerted by the piston when actuating in operative manner.

In a particular embodiment, the system further comprises a collecting compartment provided beneath the membrane structure and configured for receiving:
  rock sample particles produced during the sand production test; and
  the second fluid passing through the rock sample during the sand production test.

In a particular embodiment, a section of the collecting compartment comprises a sand deflector, said sand deflector comprising a plate fixed to an inner face of the collecting compartment, and sloping down to the lower base of the collecting compartment.

Said san deflector permits collapsing sand to fall to the lower sections of the collecting compartment in a controlled manner so as to distribute evenly at a lower base, that is, without agglomerating at the base in such a way that aggregates are formed.

In a particular embodiment, the collecting compartment comprises weighing means configured for receiving and weighing the rock sample particles produced during the sand production test.

In a particular embodiment, the weighing means comprise a load cell coupled to a collecting plate located at a lower section of the collecting compartment.

In a particular embodiment, the first base plate comprises at least one extensometer which, in turn, comprises an elastically deformable support structure facing the at least one radial hole housing a pin, such that:

the elastically deformable support structure comprises a strain gauge, and the pin is coupled by one end to the support structure.

As aforementioned, the pins housed within can move linearly due to the displacement of the sample of rock caused by its deformation, being able to transmit the movement to an extensometer shaped as a a flexible column-type support structure which comprises a strain gauge. According to this configuration, the pin is pushed against the sample of rock and the movement of the pin follows the displacement of the sample of rock at the contact location. The strain gauge generates a signal proportional to the displacement of the ping and therefore to the displacement of the sample of rock allowing to determine its deformation.

In a particular embodiment, at least one of the openings of the radial holes provided at the watertight outer wall comprise a flexible centering bushing.

DESCRIPTION OF THE DRAWINGS

These and other features and advantages of the invention will be seen more clearly from the following detailed description of a preferred embodiment provided only by way of illustrative and non-limiting example in reference to the attached drawings.

DETAILED DESCRIPTION OF THE INVENTION

Once the object of the invention has been outlined, specific non-limitative embodiments are described hereinafter.

Figure 1:
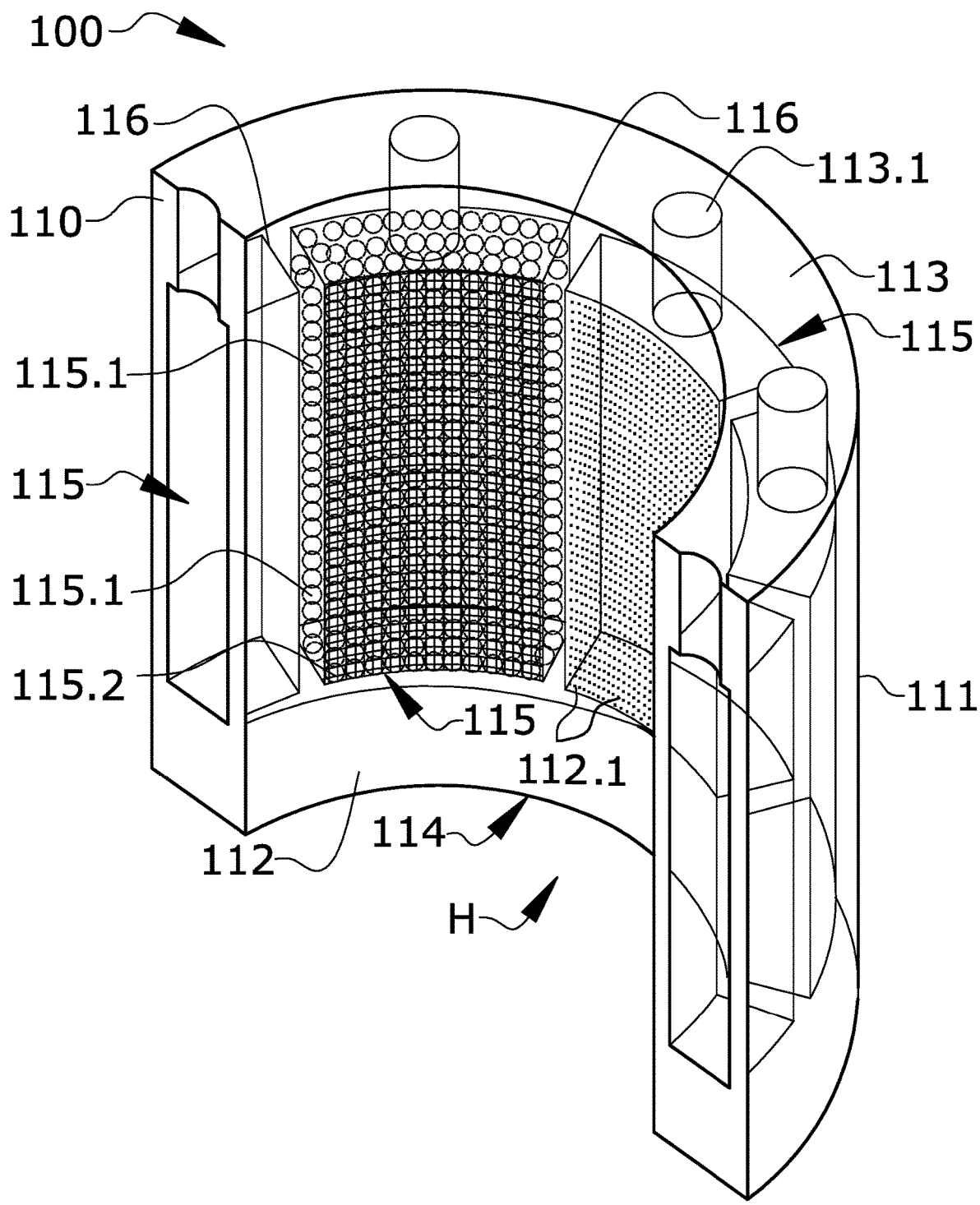
FIG. 1 This figure shows an embodiment of a membrane structure according to the invention, intersected by a vertical plane passing through a diameter, showing details of the internal hollow chambers.

FIG. 1 depicts an embodiment of a membrane structure (100) suitable for a sand production test of a rock sample (300), according to the invention. The membrane structure (100) comprises a main body (110) provided with a hollow cylinder shape extending along a longitudinal direction.

The main body (110) is shown intersected by a vertical plane passing through a diameter for showing details of internal parts of the membrane structure (100). In particular, the main body (110) is provided with such an annular cylindrical shape in order to house the rock sample (300) within, which is also provided with a hollow cylinder shape. No rock sample (300) is shown in FIG. 1, and so part of the internal volume of the main body (110) is shown. In particular, said inner volume configured to confine the rock sample (300) within is defined as the housing referred to with reference (H).

Additionally, the main body (110) of the membrane structure (100) comprises a watertight outer wall (111) adapted to withstand external hydrostatic pressure exerted by a first fluid when the membrane structure (100) is in operative manner. In particular, during a sand production test, the membrane structure (100) is part of a sanding cell upon which external forces are applied in order to simulate real conditions of a borehole. In this sense, the sanding cell, i.e., the membrane structure (110) will be confined within a close chamber filled with a pressure oil (i.e., the first fluid) which will apply an hydrostatic pressure on the watertight outer wall (111) of the main body (110), a pressure that the main body (110) of the membrane structure (100) must transmit to the rock sample (300) confined within the housing (H).

With regards to the internal boundary of the membrane structure (100), the main body (110) comprises a permeable inner wall (112) limiting the housing (H) and configured to exert pressure on the rock sample (300) and, to inject a second fluid into the outer surface of said rock sample (300) when the membrane structure (100) is in operative manner.

Said second fluid is provided and housed within a plurality of internal hollow chambers (115) located between the watertight outer wall (111) and the permeable inner wall (112). In particular, the membrane structure (100) shown comprises eight internal hollow chambers (115) equidistributed along a circular path around the longitudinal direction. It can be regarded as a whole void annulus which is divided into separate chambers (115) which extend along circular trapezoidal sections of equal size.

For separating each internal hollow chamber (115) from adjacent ones, the main body (110) comprises a plurality of partition walls (116), each one of the plurality of partition walls (116) thus being configured for separating two adjacent internal hollow chambers (115). In particular, the main body (110) of the membrane structure (100) shown comprises eight partition walls (116).

With regards to the aforementioned pressure exerted by the permeable inner wall (112) it is the total result of the partial contribution of the hydrostatic pressure exerted by the first fluid on the watertight outer wall (111) plus the differential pressure applied by each portion of the permeable inner wall (112) corresponding to the circular sector wherein an internal hollow chamber (115) is located.

More in particular, the permeable inner wall (112) allows the second fluid housed in each internal hollow chamber (115) to flow under pressure onto the rock sample (300) housed within the housing (H) of the main body (110). Accordingly, it is possible to apply different pressure on specific peripheral portions of the rock sample (300) thanks to the operational independence of each internal hollow chamber (115) with respect to the others. Therefore, flowing the second fluid flowing through each internal hollow chamber (115) at different pressures in order to apply different pressure on specific portions of the rock sample (300) provides the capability of performing a pluriaxial (or true triaxial) test.

Additionally, the main body comprises a first base (113) and a second base (114) opposite to the first base (113) according to the longitudinal direction.

For the supply of the second fluid to each one of the internal hollow chambers (115), the first base (113) of the main body (110) comprises a plurality of inlets (113.1), each one being configured for establishing a fluidic communication between each internal hollow chamber (115) and an external source of the second fluid.

Finally, each internal hollow chamber (115) comprises a plurality of rigid particles (115.1) filling the inner space. Said plurality of rigid particles (115.1) bridge the watertight outer wall and the permeable inner wall (112) so as to transmit the hydrostatic pressure exerted by the first fluid between them, while leaving empty interstices among them so as to let the second fluid access each hollow chamber (115). For illustrative purposes, only one internal hollow chamber (115) is shown comprising a plurality of rigid particles (115.1).

Figure 2:
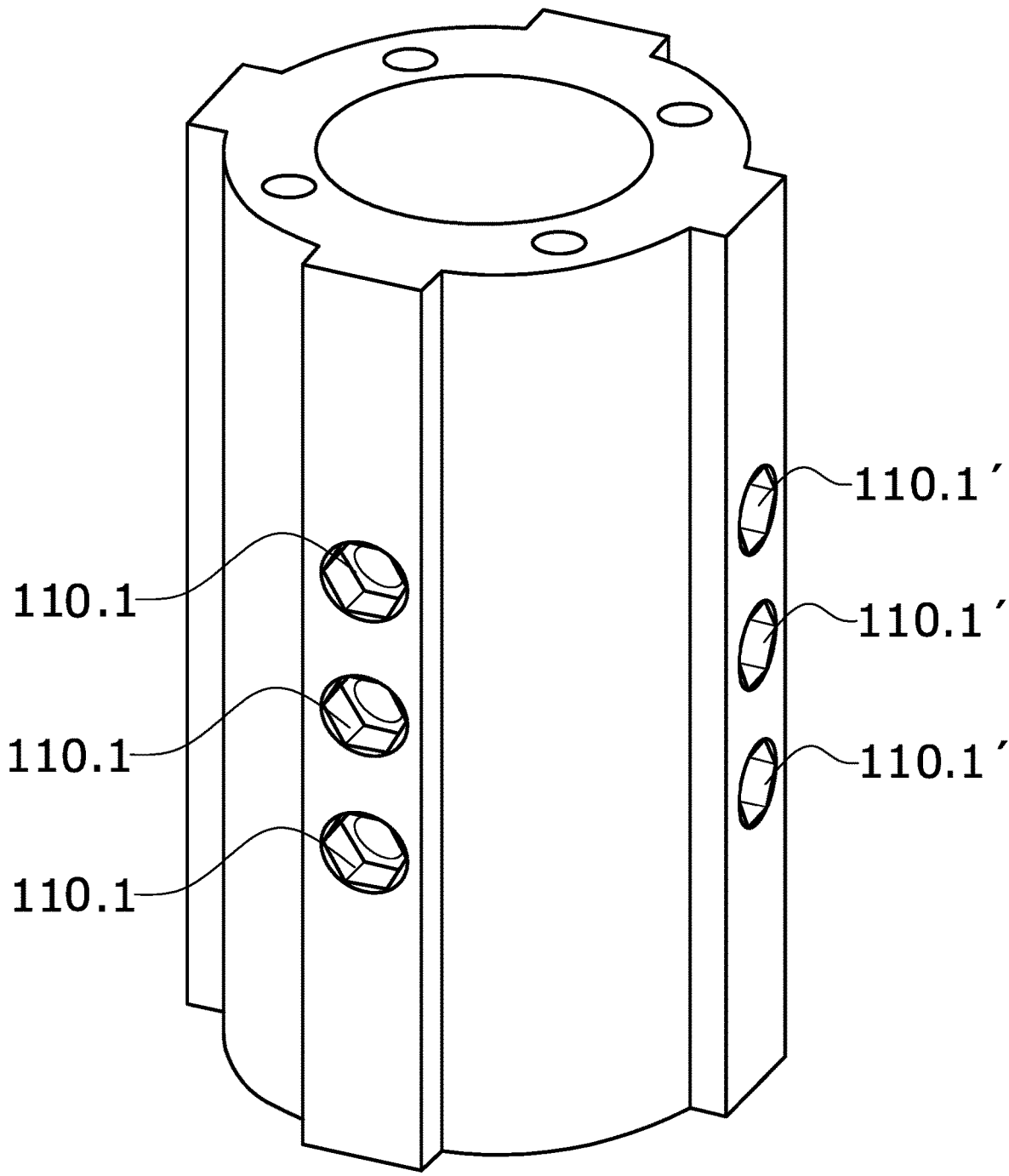
FIG. 2 This figure shows an enhanced view of an embodiment of a membrane structure according to the invention, the membrane being implemented in a sand production system between a first and a second base plate.

FIG. 2 shows an enhanced view of a membrane structure (100) implemented in a system suitable for a sand production test, between a first and a second base plate. The membrane structure (100) shows two rows of respective trios of radial holes (110.1, 110.1') provided on the watertight outer wall (111) of the main body (110). These radial holes (110.1, 110.1') are configured to house a pin connected to an extensometer, allowing the access of the pin through respective openings provided at the watertight outer wall (111) to the inner wall for measuring the radial deformation of the rock sample.

In particular, the two rows of radial holes (110.1, 110.1') are provided at respective prismatic protrusions which extend from the watertight outer wall (111) of the main body (110), for providing an easier access to the radial holes (110.1, 110.1') from the outside for the insertion of each pin.

Figure 3:
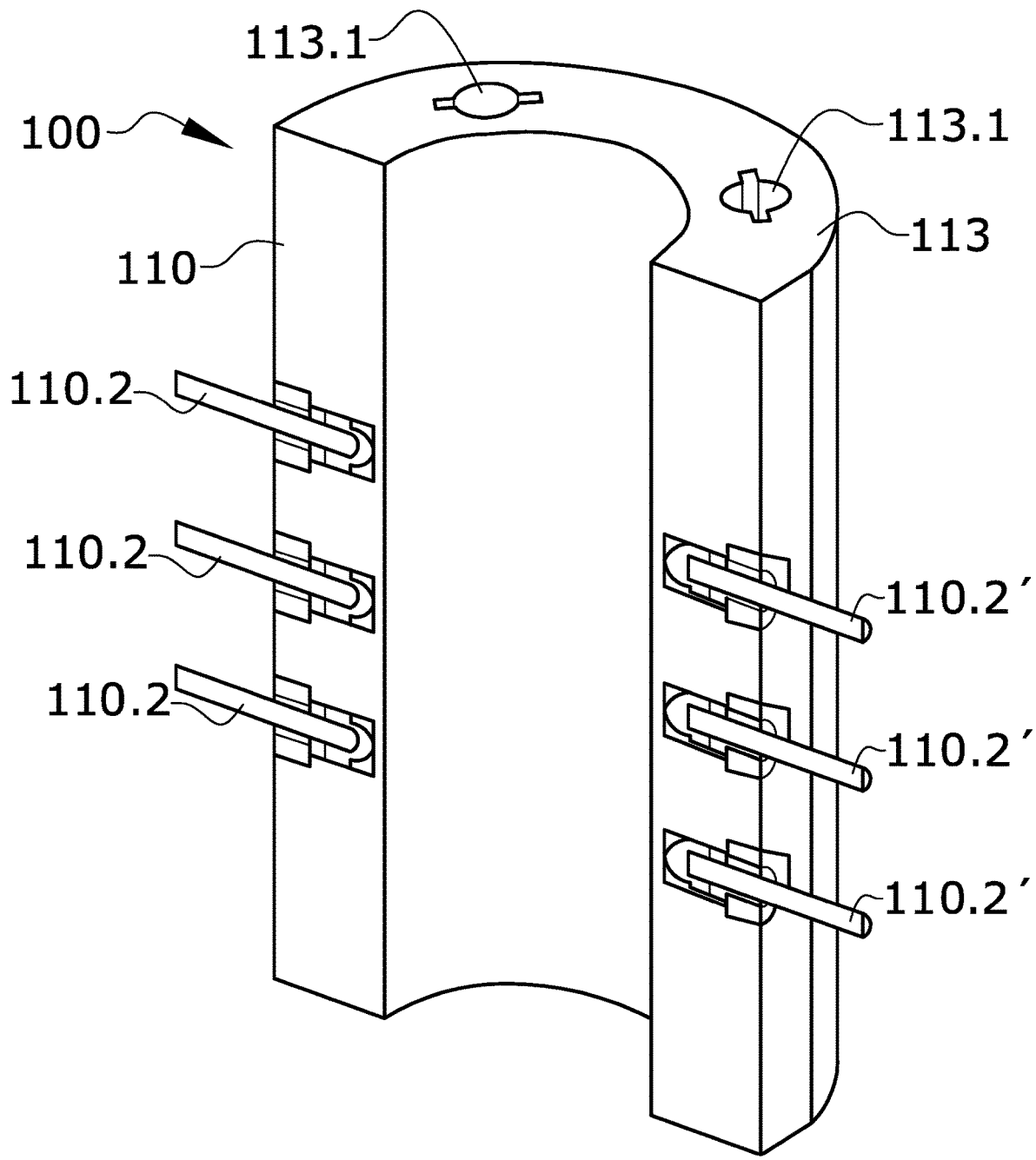
FIG. 3 This figure shows an embodiment of a membrane structure according to the invention, intersected by a vertical plane passing through a diameter wherein the main body of the membrane structure comprises two rows of radial holes, each one housing a respective pin of an extensometer.
Figure 4:
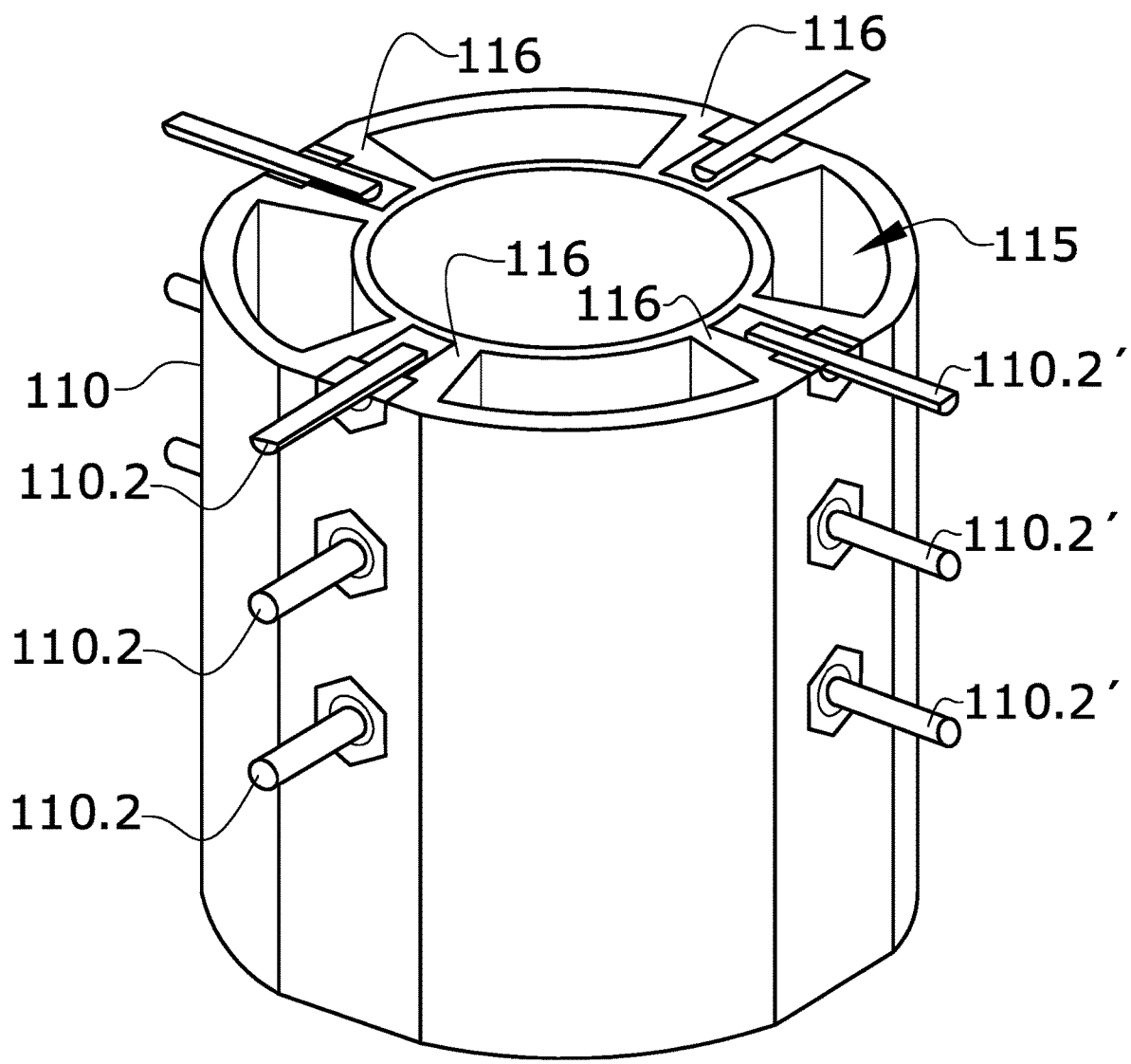
FIG. 4 This figure shows an embodiment of a membrane structure according to the invention wherein the main body of the membrane structure comprises four rows of radial holes, each one housing a respective pin of an extensometer.

FIGS. 3 and 4 show different perspectives of an embodiment of a membrane structure (100), wherein the main body (110) of the membrane structure (100) comprises several rows of radial holes, each one housing a respective pin (110.2, 110.2') of an extensometer.

On one side, FIG. 3 is intersected by a vertical plane passing through a diameter of the hollow cylindrical shape of the main body (110) of the membrane structure (100), so that only one half of the main body (110) is shown. It can be seen how the pins (110.2, 110.2') access through respective openings provided at the watertight outer wall, as well as how each row of pins (110, 110.2') is housed within internal channels extending through corresponding partition walls (116). Said channels comprise a distal end located proximate to the rock sample, that is, in a circular section of the main body (110) with a radius slightly greater than the radius of the permeable inner wall.

Unlike FIG. 1, FIG. 3 does not provide details of the internal hollow chambers (115). Only two inlets (113) can be seen provided at the first base (113), each inlet (113) corresponding to a respective internal hollow chamber (115) located within the main body (110). Accordingly, the membrane structure (100) comprises four internal hollow chambers (115), as can be seen in FIG. 4.

On the other side, FIG. 4 intersected by a horizontal plane which cuts the uppermost of the three pins (110.2, 110.2') in half, so that additional details are shown regarding how the pins (110.2, 110.2') access the near-rock sample region, through the partition walls (116), for measuring rock sample deformations. In particular, it is seen how the distal end of the internal channels is located before a cylindrical section corresponding to the permeable inner wall (112).

In this way, the distal end of the pins (110.2, 110.2') mechanically contact the near-rock sample region of the membrane structure (100) for measuring deformations of the outer surface of the rock sample during the sand production test.

Accordingly, these deformations are translated into linear displacements of the pins (110.2, 110.2') housed within the radial holes. Therefore, the pins (110.2, 110.2') move linearly, being able to transmit said movement to an extensometer mounted on a column-type support structure, located facing each row of pins (110.2, 110.2'), thus providing information related to the deformation of the rock sample in the form of an electrical variation.

Figure 5:
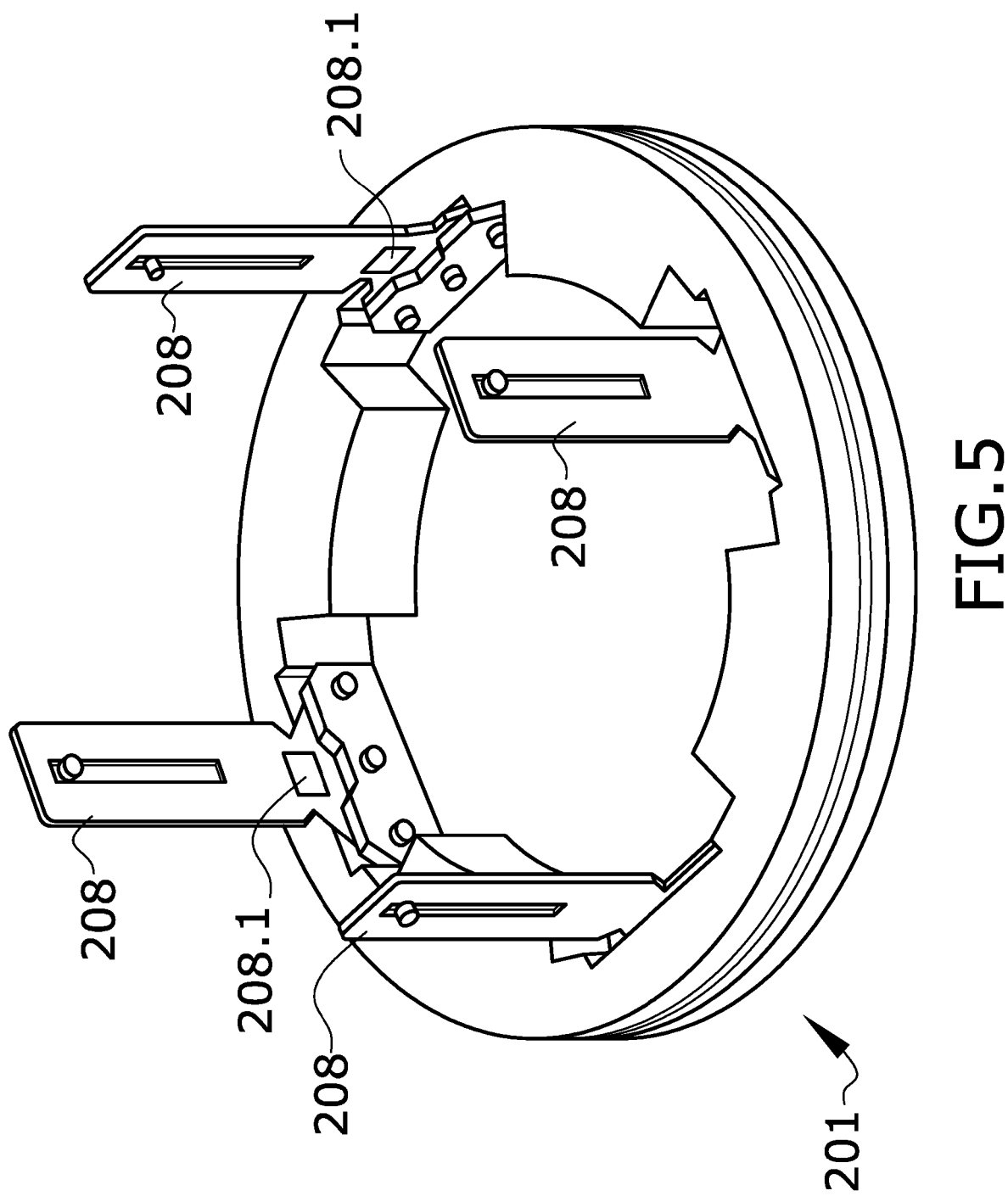
FIG. 5 This figure shows a schematic representation of an array of elastically deformable support structures for a system suitable for a sand production test, according to the invention.

Additionally, as can be seen in both FIGS. 3 and 4, the openings of the radial holes are provided with respective flexible centering bushings configured to provide the pins (110.2, 110.2') with better alignment and accommodation within the radial holes FIG. 5 shows a schematic representation of an array of four elastically deformable support structures (208), which are part of four respective extensometers, for a system suitable for a sand production test, according to the embodiments shown in FIGS. 3 and 4. In particular, it is seen how a portion of a structure of a first base plate (201) comprises four column-type support structures (i.e., the elastically deformable support structures (208)), each one disposed so as to face a respective row of the radial housing the pins (110.2, 110.2') shown in FIGS. 3 and 4.

According to this configuration, each of the elastically deformable support structures (208) of the extensometers, comprises a strain gauge (208.1), with each pin (110.2, 110.2') being coupled by one end to said elastically deformable support structure (208) too. In a preferred embodiment, at least one of the elastically deformable support structures (208) comprises two strain gauges (208.1) arranged according to a half (Wheatstone) bridge configuration. In another preferred embodiment, at least one of the elastically deformable support structures (208) comprises four strain gauges (208.1) arranged according to a full (Wheatstone) bridge configuration.

Figure 6:
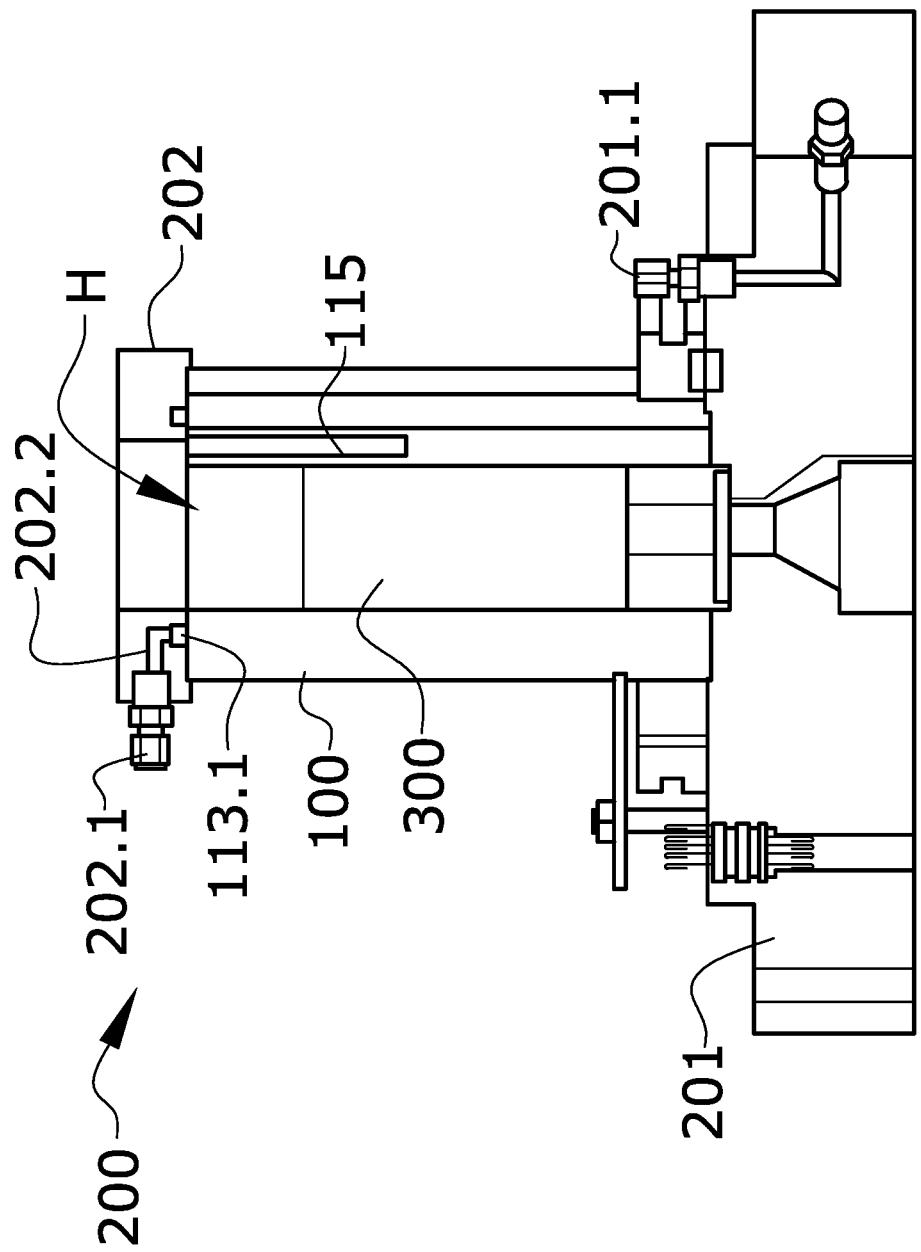
FIG. 6 This figure shows a front view of an embodiment of a system suitable for a sand production test according to the invention, intersected by a vertical plane.
Figure 7:
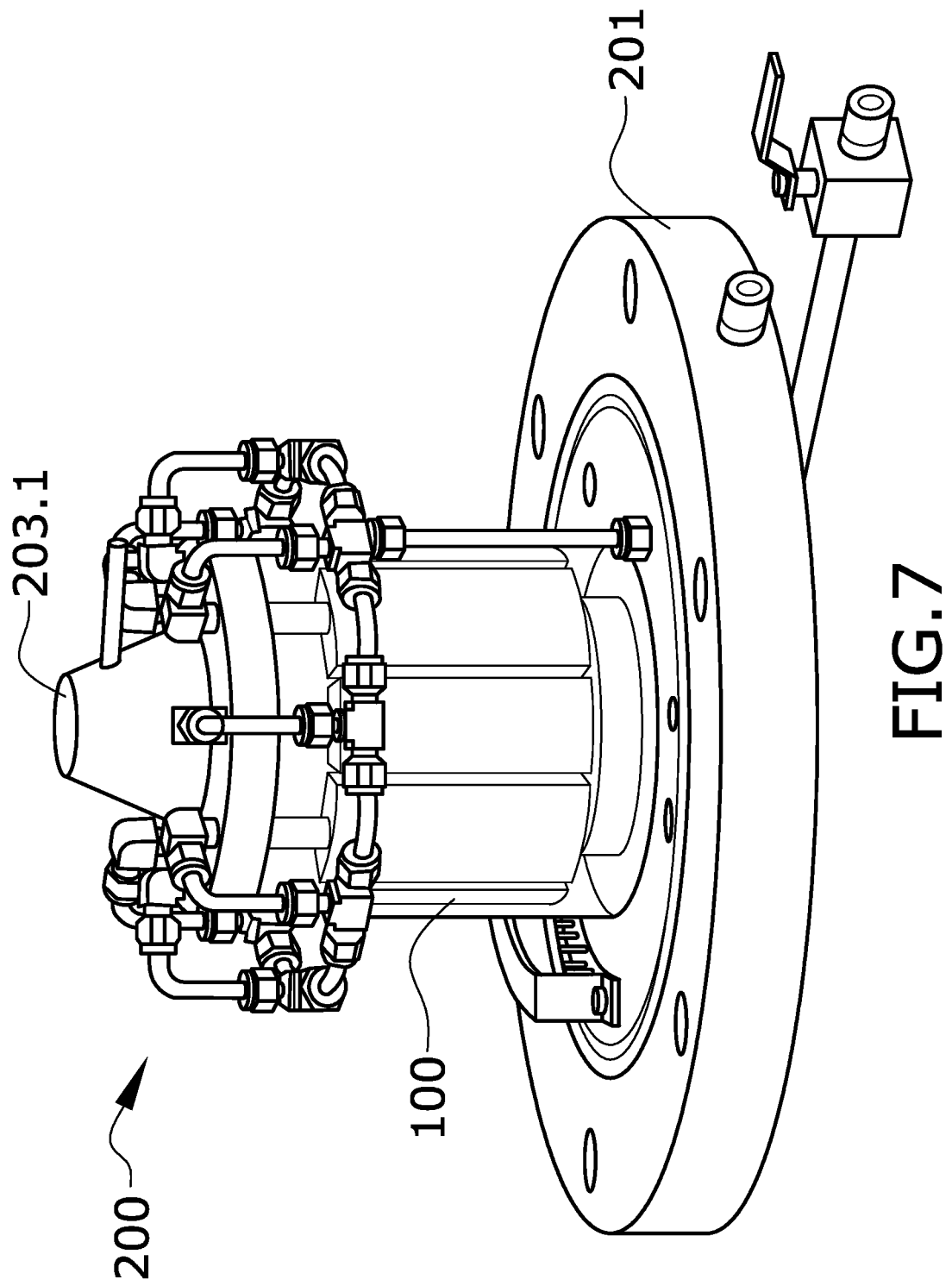
FIG. 7 This figure shows a perspective view of an embodiment of a system suitable for a sand production test according to the invention.
Figure 8:
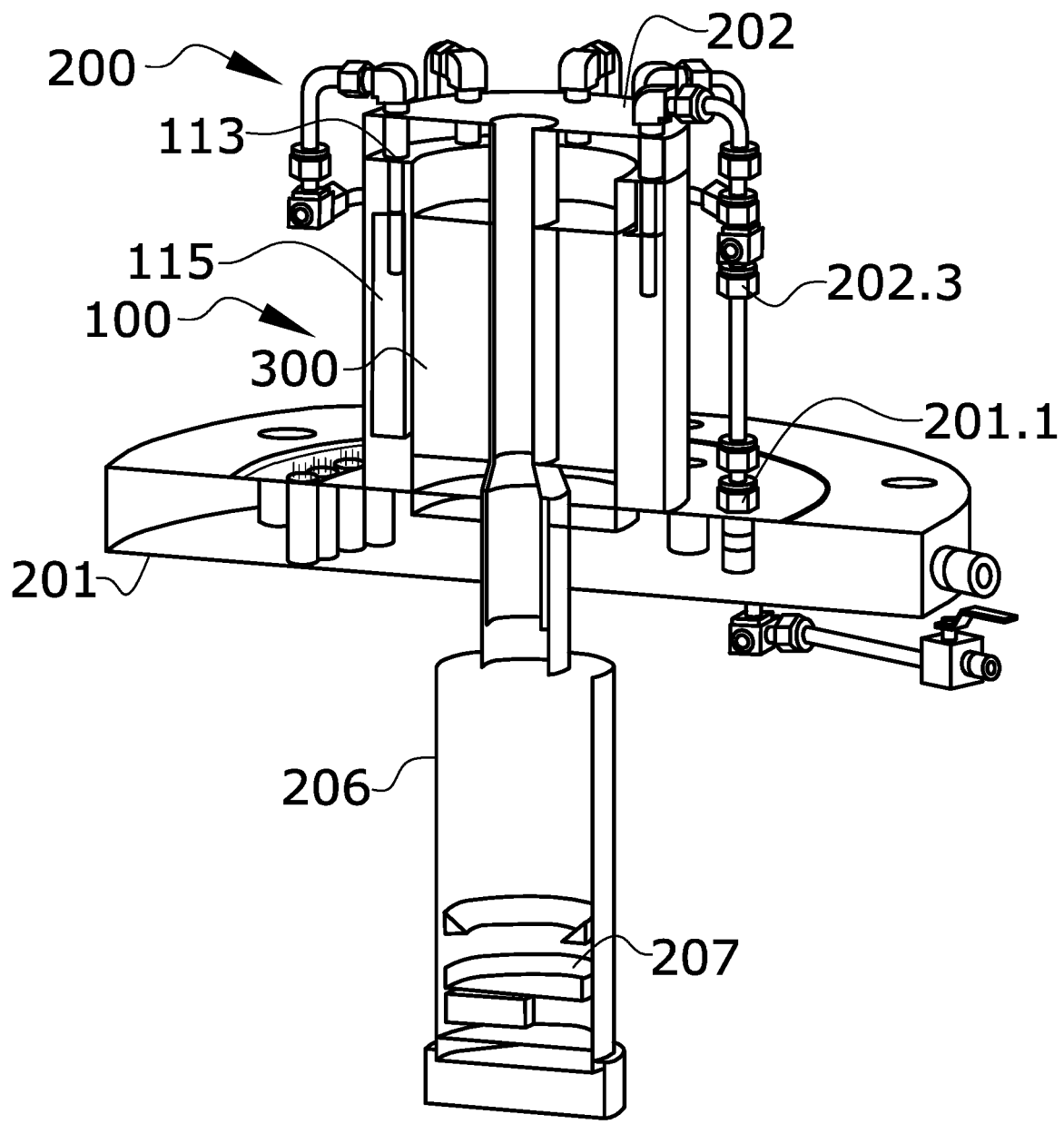
FIG. 8 This figure shows a perspective view of an embodiment of a system suitable for a sand production test according to the invention, intersected by a vertical plane, the system comprising a collecting compartment.

FIGS. 6, 7 and 8 show different configurations of a system (200) suitable for a sand production test according to the invention.

In particular, FIG. 6 shows a front view of the system (200), intersected by a vertical plane which provides view of internal details of the system (200). As can be seen, the system (200) comprises a first base plate (201) onto which the rest of the elements of the system (200) shown are resting.

A membrane structure (100) according to an embodiment of the first inventive aspect is fixed by its lower (i.e., second) base to the first base plate (201). A rock sample (300) provided with a hollow cylinder shape is provided within the internal housing (H) of the membrane structure (100). A second base plate (202) is shown resting on the upper (i.e., first) base of the membrane structure (100), closing said housing (H).

With respect to the distribution of the first and second fluid used for application of axial pressure on the rock sample (300) during the sand production test, the system (200) of FIG. 6 comprises the following elements.

Regarding the supply of the first fluid, that is, the fluid used to apply hydrostatic pressure on the watertight outer wall of the membrane structure (100), the system (200) comprises a first pump (not shown) for pumping the first fluid into the intermediate space of the casing (not shown) for increasing the first fluid pressure.

With respect to the distribution of the second fluid, that is, the fluid supplied inside the internal hollow chambers (115) for later supply under pressure onto the rock sample (300), the system (200) comprises a second pump (not shown) for pumping the second fluid. Additionally, it can be seen that the second base plate (202) comprises an input port (202.1) for the intake of the second fluid; and an output port (202.2) which is shown in fluidic communication with an inlet (113.1) of the membrane structure (100) for providing a corresponding internal hollow chamber (115) with a flow of the second fluid.

The fluid communication between the second pump and the input port (202.1) of the second base plate (202) is established by means of a distribution piping (which is shown in FIGS. 7 and 8), such that said distribution piping (202.3) is coupled at a first end with the input port (202.1) of the second base plate (202); and at a second end with a second input port (201.1) provided at first base plate (201).

FIG. 7 shows a perspective view of the whole system (200) of FIG. 6, wherein the distribution piping (202.3) has been represented. In particular, it can be seen that the inlet port (201.1) of the first base (201) is connected to a single duct which is connected, downstream of the inlet port (201.1) with a distribution ring comprising a plurality of ducts, each of them coupled by an end with a respective input port (202.1) of the second base plate (202) for establishing fluidic communication. In turn, each input port (202.1) of the second base plate (202) is in fluidic communication with a respective output port (202.2) which, in the same manner, finally establish fluidic communication with one of the inlets (113.1) provided at the first base (113) of the membrane structure (100) for providing a flow of the second fluid to a corresponding internal hollow chamber (115).

Additionally, the system (200) shown in FIG. 7 comprises a portion of a piston (203) adapted to exert axial force to the second base plate (202) according to the longitudinal direction. In particular, it can be seen that a truncated cone (203.1) is resting on the second base plate (202) for distributing the pressure, to the second base plate (202), of the axial force exerted by the piston when actuating in operative manner. According to another embodiment, the truncated cone (203.1) is replaced by a cylinder.

FIG. 8 shows a perspective view of the system (200) of FIG. 7, intersected by a vertical plane which provides view of internal details of the system (200), and further comprising a collecting compartment (206) provided beneath the membrane structure (100) and configured for receiving both the rock sample (300) particles produced during the sand production test; and the second fluid passing through the rock sample during the sand production test.

As can be seen, the collecting compartment (206) is provided with a tubular shape, with a lower section of the collection compartment (206) comprising a sand deflector. In particular, said sand deflector consist of a curved plate fixed to an inner face of the collecting compartment (206) sloping down to the lower base of the collecting compartment (206), so as to permit collapsing sand to fall to the lower sections of the collecting compartment (206) in a controlled manner and try to prevent it from agglomerating at the base in such a way that aggregates are formed.

Additionally, the collecting compartment (206) comprises weighing means (207) configured for receiving and weighing the rock sample (300) particles produced during the sand production test and deflected by the sand deflector. In particular, the weighing means (207) comprise a load cell coupled to a collecting plate located at a lowermost section of the collecting compartment (206).

Figure 9:
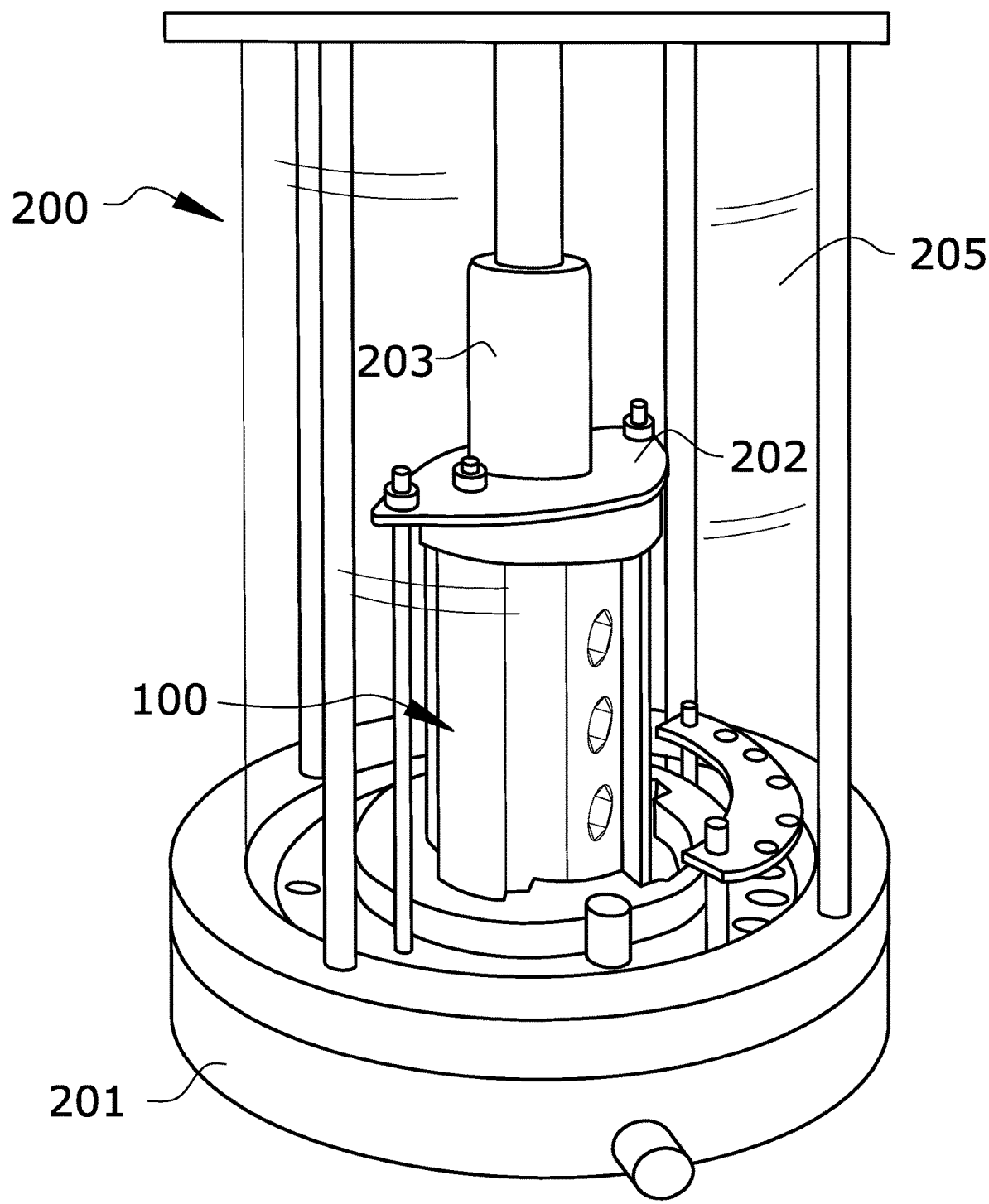
FIG. 9 This figure shows a perspective view of an embodiment of a system suitable for a sand production test according to the invention.

FIG. 9 shows a perspective view of an embodiment of a system (200) suitable for a sand production test fully assembled in an operative configuration. In particular, it can be seen that one of the system (200) arrangements shown in FIG. 6, 7 or 8 is confined within a casing (205) which is arranged so as to be watertightly fixed on the first base plate (201), defining a pressure chamber within, that is, an intermediate space between the casing (205) and the membrane (100). This intermediate space is configured for housing the first fluid supplied by the first pump so as to exert a predetermined hydrostatic pressure on the membrane structure (100).

The invention claimed is:

1. A membrane structure suitable for a sand production test of a rock sample provided with a hollow cylinder shape extended along a longitudinal direction, the membrane structure comprising a main body, wherein the main body comprises:
   a housing configured to confine the rock sample within;
   a watertight outer wall adapted to withstand external hydrostatic pressure exerted by a first fluid when the membrane structure is in operative manner;
   a permeable inner wall limiting the housing and configured to exert pressure on the rock sample and, to inject a second fluid into the outer surface of said rock sample when the membrane structure is in operative manner;
   a first base;
   a second base opposite to the first base according to the longitudinal direction;
   a plurality of internal hollow chambers located between the watertight outer wall and the permeable inner wall, wherein
   the main body of the membrane structure comprises a plurality of partition walls, each one of the plurality of partition walls being configured for separating two adjacent internal hollow chambers;
   the first base or the second base of the main body comprises a plurality of inlets, each one being configured for establishing a fluidic communication between one of the plurality of internal hollow chambers and an external source of the second fluid; and each one of the plurality of internal hollow chambers comprises a plurality of rigid particles filling the inner space of each hollow chamber, said plurality of rigid particles intended for transmitting the external pressure exerted from the watertight outer wall to the permeable inner wall while allowing the passage of the second fluid from the at least one of the plurality of inlets to the permeable inner wall.

2. The membrane structure according to claim 1, wherein at least one of the plurality of internal hollow chambers extends along a circular trapezoidal section of the main body.

3. The membrane structure according to claim 1, wherein the permeable inner wall comprises a plurality of pores such that fluidic communication is established between each one of the plurality of internal hollow chambers and the housing configured to confine the rock sample.

4. The membrane structure according to claim 1, wherein the plurality of internal hollow chambers is equidistributed along a circular path around the longitudinal direction.

5. The membrane structure according to claim 1, wherein the plurality of rigid particles are steel spherical particles stacked in a close-packing configuration.

6. The membrane structure according to claim 1, wherein at least one internal hollow chamber comprises a filtering mesh provided next to the permeable inner wall.

7. The membrane structure according to claim 1, wherein the main body comprises at least one radial hole configured to house a pin connected to an extensometer, allowing the access of the pin through an opening provided at the watertight outer wall to the permeable inner wall for measuring the radial deformation of said rock sample.

8. The membrane structure according to claim 7, wherein the radial hole extends through a partition wall of the main body.

9. The membrane structure according to claim 1, wherein the main body is made of an elastomeric polymer.

10. A system suitable for a sand production test of a rock sample provided with a hollow cylinder shape extended along a longitudinal direction, the system comprising:
    a first base plate;
    a membrane structure according to claim 1, the second base of the membrane structure resting on the first base plate;
    a second base plate resting on the first base of the membrane structure configured for exerting axial force to the membrane structure and to the rock sample confined within the housing of the membrane structure in operative manner;
    a casing located over the first base plate, the casing configured for housing the membrane structure and the second base plate with an intermediate space between the casing and the membrane structure for housing the first fluid;
    a piston adapted to exert axial force to the second base plate according to the longitudinal direction;
    a first pump for pumping the first fluid;
    a second pump for pumping the second fluid;
    wherein the second base plate comprises at least an input port for the second fluid and an output port for the second fluid, such that
        the input port is in fluidic communication with the second pump; and
        the output port is in fluidic communication with at least one inlet of the membrane structure configured for establishing a fluidic communication between the plurality of internal hollow chambers and an external source of the second fluid; and
    wherein the first pump is in in fluid communication with the intermediate space of the casing for increasing a first fluid pressure, the first fluid being in contact with the watertight outer wall of the membrane structure in operative manner.

11. The system according to claim 10, wherein the fluid communication between the second pump and the input port of the second base plate is established by means of a distribution piping, such that
    the distribution piping is coupled at a first end with the input port of the second base plate; and
    the distribution piping is coupled at a second end with the first base plate;
and wherein the first base plate further comprises a second input port configured for establishing fluid communication between the second pump and the second end of the distribution piping.

12. The system according to claim 10, wherein the piston is coupled to a truncated cone resting on the second base plate and configured for pressure redistribution, to the second base plate, of the axial force exerted by the piston when actuating in operative manner.

13. The system according to claim 10, further comprising a collecting compartment provided beneath the membrane structure and configured for receiving:
    rock sample particles produced during the sand production test; and
    the second fluid passing through the rock sample during the sand production test.

14. The system according to claim 13, wherein the collecting compartment comprises weighing means configured for receiving and weighing the rock sample particles produced during the sand production test.

15. The system according to claim 10,
    wherein the main body of the membrane structure comprises at least one radial hole configured to house a pin connected to an extensometer, allowing the access of the pin through an opening provided at the watertight outer wall to the permeable inner wall for measuring the radial deformation of said rock sample, and
    wherein the first base plate comprises at least one extensometer which, in turn, comprises an elastically deformable support structure facing the at least one radial hole housing the pin, such that:
        the elastically deformable support structure comprises a strain gauge, and
        pin is coupled by one end to the support structure.

* * * * *